(12) United States Patent
Kimberly

(10) Patent No.: US 6,664,052 B1
(45) Date of Patent: Dec. 16, 2003

(54) GENETIC POLYMORPHISM IN A COMPLEMENT RECEPTOR

(75) Inventor: Robert P. Kimberly, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/744,346

(22) PCT Filed: Jul. 23, 1999

(86) PCT No.: PCT/US99/16264

§ 371 (c)(1),
(2), (4) Date: Mar. 23, 2001

(87) PCT Pub. No.: WO00/05413

PCT Pub. Date: Feb. 3, 2000

Related U.S. Application Data

(60) Provisional application No. 60/106,643, filed on Nov. 2, 1998, and provisional application No. 60/094,096, filed on Jul. 24, 1998.

(51) Int. Cl.[7] ................................................ C12Q 1/68
(52) U.S. Cl. .......................................... 435/6; 530/350
(58) Field of Search ................................ 435/6; 530/350

(56) References Cited

U.S. PATENT DOCUMENTS 5,426,029 A    6/1995  Rittershaus et al.

FOREIGN PATENT DOCUMENTS

WO    WO89/09220    10/1989

OTHER PUBLICATIONS

Kumar, A. et al., HindIII genomic polymorphis of the C3b receptor (CR1) in patients with SLE, Immunology and Cell Biology, Jun. 5, 1995, vol. 73, pp. 457–462.

Carroll, M.C., The Role of Complement and Complement Receptors in Induction and Regulation of Immunity 1998, vol. 16, pp. 545–568.

*Primary Examiner*—James Ketter
(74) *Attorney, Agent, or Firm*—Gifford, Krass, Groh, Sprinkle, Anderson, & Citkowski, P.C.

(57) ABSTRACT

A method and a package for identifying single nucleotide polymorphisms in complement receptor is useful in identifying individual susceptibility to a disease. Complement receptors CR1 and CR2 are active in the immune response and autoimmune diseases. The susceptibility and severity of autoimmune disease is determined by genotyping or phenotyping an individual for complement receptor.

5 Claims, 1 Drawing Sheet

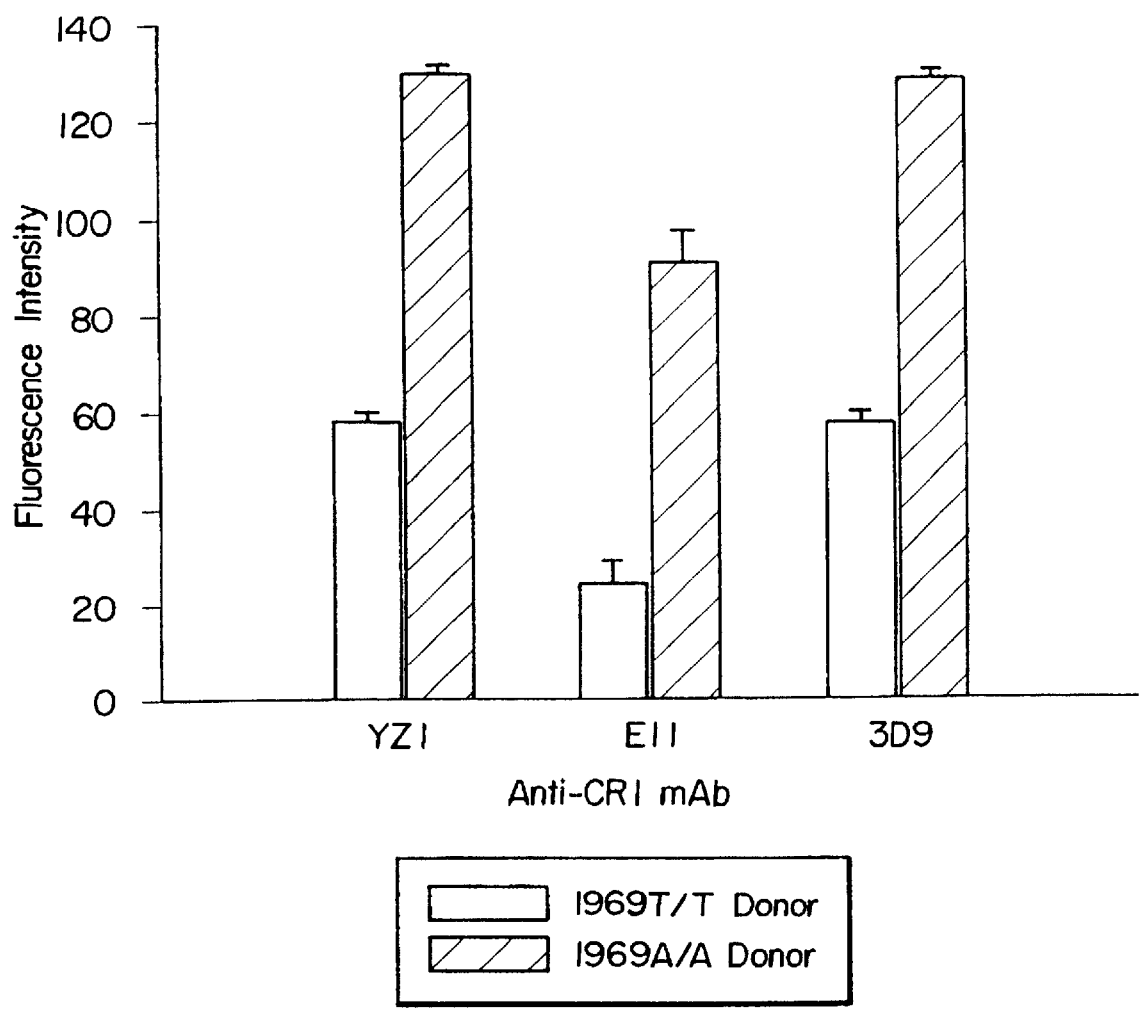

GENETIC POLYMORPHISM IN A COMPLEMENT RECEPTOR

RELATED APPLICATIONS

This patent application is based on U.S. provisional application Ser. No. 60/094,096 filed Jul. 24, 1998 entitled "Genetic Polymorphism in the Receptor for IgA," and U.S. provisional application Ser. No. 60/106,643 filed Nov. 2, 1998 entitled "Genetic Polymorphism in a Complement Receptor."

GRANT REFERENCE

The subject invention was made with government support from the National Institutes of Health (NIH 1 P50 AR45231-01). The government has certain rights in the invention.

FIELD OF THE INVENTION

The present invention relates generally to compounds and methods for identifying polymorphism in a cellular receptor, and more particularly, to compounds and methods for identifying and typing single nucleotide polymorphisms that code for a complement receptor and applying these polymorphisms to delineation of disease susceptibility and severity.

BACKGROUND OF THE INVENTION

The complement system involves a group of proteins that play a role in host defense against infection. Complement is active in immune defenses, especially antibody mediated events by way of the "classical pathway." Complement response to an invasion by a foreign particle can also embody an antibody independent mechanism which is known as the "alternative pathway."

As part of the body's natural defenses, the complement system operates as a biological cascade in which one component activates successive components. Activation is usually by way of a proteolytic cleavage event. The complement system functions to promote the inflammatory response, to modify the membranes of infectious organisms, and also to identify pathogenic material for removal.

The inflammatory response is triggered by way of the cascade, in which low molecular weight peptides are cleaved from complement proteins. The resulting anaphylatoxins and chemotactic factors attract leukocytes and modify vascular permeability.

The attachment of complement proteins, C3b/C4b to microbial membranes or immune complexes, a process commonly known as opsonization, facilitates the binding of opsonized material to cell receptors. By modifying the membranes of a microbe, complement also participates directly in microbial destruction.

Immune complex opsonization enables the process in which specific receptors on a cell bind complement components. In some cases this binding process leads to phagocytosis of the complement bound antigen particles. The primary opsonins of the complement system are C3b and C4b which are activated by cleavage of fragments C3 and C4. C3b and C4b are capable of covalently binding to foreign antigen particles. The resulting C3b/C4b coded complexes are ligands for the C3b/C4b receptor on human peripheral blood cells. The C3b/C4b receptor is also known as complement receptor 1 (CR1).

Receptors for complement proteins function to bind complement coated antigens. CR1 is present on most peripheral blood cells, including erythrocytes, B lymphocytes, granulocytes, monocytes, neutrophils and some T cells. Erythrocyte CR1 upon binding the C3b/C4b immune complex conveys the immune complex to the liver or spleen where the ligand is transferred to hepatic macrophages for internalization and disposal. As a result, CR1 plays a role in neutralizing complement activated immune complexes within the body. Thus, defects in this receptor are associated with impaired phagocytosis and can lead to enhanced destructive processes such as joint destruction in rheumatoid arthritis, and impaired host defense against infection.

The role of complement receptor 2 (CR2) is currently not fully understood. Nonetheless, CR2 binds activated complement components and is operative in response to foreign particles.

Autoimmune diseases are often characterized by abnormal deposits of complement fixing immune complexes. Such deposits may result from excessive immune complex formation, inappropriate antibody production illustratively including IgG, IgM and IgA, complement deficiencies or receptor anomalies. Receptors that are incapable of binding and/or releasing immune complex or that are underexpressed on the cell surface would result in incomplete removal of immune complexes thereby resulting in deposition.

Such abnormal deposits are associated with a variety of diseases including several types of human glomerulonephritis. In particular, systemic lupus erythematosus (SLE) is associated with glomerular deposits of early complement cascade components such as C1q, C4 and C2. Deposition of these components is suggestive of the classical pathway of complement activation in this disease. Other types of glomerulonephritis such as IgA neuropathy, bacterial infections and membranoproliferative glomerulonephritis are typically associated with glomerular deposits of C3 and properdin, thus suggesting alternative pathway dysfunction in these diseases. The CR1 receptor in humans and primates is found on most types of peripheral blood leukocytes and erythrocytes, however not on platelets. Due to the large fraction of erythrocytes in blood, a great majority of all CR1 in peripheral blood is found on erythrocytes. Perhaps greater than 90% of all CR1 is found on erythrocytes. The characterization of CR1 has previously failed to make a definitive correlation between CR1 structure and immunological disease severity.

CR1 is a single polypeptide chain that exhibits a size polymorphism derived from four codominant inherited alleles. The alleles are: type A (220 kD), type B (250 kD), type C (190 kD) and type D (280 kD). These four alleles result in ten phenotypes of CR1 within the human population which have varying numbers of C3b binding sites. Fluctuations in erythrocyte CR1 expression associated with SLE progression suggests that genetic predisposition as to size polymorphism is not a controlling factor in SLE (Please fill in reference prop #110, now 1). While SLE is an important autoimmune disease, fluctuating levels of CR1 are also associated with diseases including hemolytic anemias, AIDS, rheumatoid arthritis, Sjogren's syndrome and lepromatous leprosy.

CR1, in addition to having the four codominant size polymorph alleles, also exhibits Knops blood group polymorphism (Please fill in reference prop #107, now 2) and cis-acting Hind III restriction fragment length polymorphism (RFLP) (Please fill in reference prop #108, now 3). Little is known about the role of the Knops antigen in receptor function and therefore its role in autoimmune diseases, such as SLE. RFLP correlates with quantitative expression of CR1 on erythrocytes. RFLP has a 6.9 kilobase polymorph which correlates with low copy number expression of CR1 on erythrocytes. The other RFLP is 7.4 kilobases in size and correlates with high numeric expression. There is a controversy as to whether or not the 6.9 kilobase RFLP is found with increased frequency in SLE patients and their relatives. Similarly, controversy persists regarding the role of size polymorphism in genetic predisposition to SLE, autoimmune and pathogenic diseases.

The present invention is based on the discovery of a novel form of polymorphism in CR1. This novel polymorphism is exploited in a testing methodology which allows for early identification of individuals susceptible to diseases associated with CR1 function, offering the possibility of early and aggressive treatment in those patients.

SUMMARY OF THE INVENTION

The present invention is a system and method for correlating the ability of binding properties of human complement receptor (CR) and cellular susceptibility to a disease by identifying a CR genotype of a cell and quantifying complement protein binding by the cell expressing the CR genotype. Thereafter, the complement protein binding by the cell and complement protein binding by a second cell expressing a second FcγRI genotype is compared.

The present invention uses a single nucleotide polymorphism or combinations thereof within a CR genotype to identify individual susceptibility to a disease.

The methods of the present invention also extend to correlating the ability of a cell to bind complement protein and cellular susceptibility to a disease through identifying a Cr phenotype of a given cell and quantifying complement protein binding by said cell. Thereafter, complement protein binding by the cell is compared to a second cell having a second CR phenotype. In particular, single nucleotide polymorphisms are responsible for genotypical and phenotypical differences in CR herein.

The present invention further includes a commercial packaging including reagents for identifying single nucleotide polymorphisms in the CR genotype or phenotype of an individual as a test to identify individual susceptibility to a disease. The reagents further include instructions for the use thereof.

BRIEF DESCRIPTION OF THE DRAWINGS

FIG. 1 is a bar graph showing the expression of CR1 on erythrocytes from CR1 genotype normal donors using fluorescence measurements associated with anti-CR1 mAb.

DETAILED DESCRIPTION OF THE INVENTION

The present invention relates to compounds and methods for identifying single nucleotide polymorphisms in the complement receptors CR1 and CR2. The single nucleotide allelic differences in a complement receptor are determined by direct DNA sequencing. It is appreciated that other techniques known to the art may also be employed, these illustratively include the use of allele specific oligonucleotides as hybridization probes and/or as primers for DNA amplification, and immunological binding of antibodies that distinguish between different polymorphic forms of the complement receptor expressed on erythrocytes.

The present invention is based on the finding that single nucleotide allelic polymorphism in a gene encoding a complement receptor results in functionally distinct gene products. The expression of a polymorphic complement receptor in an individual may have important consequences for the physiological activity of the receptor by itself, or in combination with other single nucleotide polymorphs. This in turn can effect functioning of the cell types that carry the receptor. Because of the important role of complement in the immune response, the present invention has utility as a diagnostic to identify high risk patients that warrant early and aggressive treatment. As a diagnostic for infectious disease, the present invention has utility in predicting susceptibility to specific microbes and thereby guiding the use of therapeutics. As a diagnostic for autoimmune disease, the present invention has utility in diseases illustratively including SLE, systemic vasculitis, glomerulonephritides, Sjogren's syndrome and IgA nephropathy. Identification of the appropriate allelic forms further allows for gene therapy transduction of host cells to correct hereditary limitations in the host's complement receptor genes through delivery of a translatable complement receptor gene to a defective host cell. Generally, a predominant "normal" gene of the total human population or a derivative thereof would be delivered.

The present invention provides a method for identifying the complement receptor single nucleotide allelic pattern in human patients which involves testing DNA from individual patients for the presence of different allelic variants. The present invention also encompasses the identification analysis of new single nucleotide allelic forms of complement receptor genes, the analysis being achieved using methods well known in the art, such as direct DNA sequencing; single strand conformational polymorphism analysis (SSCP); "HOT" cleavage; denaturing gradient gel electrophoresis (DVGE) and combinations thereof.

Once a new polymorphism has been identified, immunological and/or molecular biological tests are used to genotype patients for the presence or absence of a given single nucleotide polymorphism. For example, monoclonal antibodies specific to the protein encoded by a newly identified single nucleotide allele are prepared by well known methods. Such methods are described in U.S. application Ser. No. 60/094,096, filed on Jul. 24, 1998. These antibodies can be used for genotyping the patient population as described above. Alternatively, allele specific oligonucleotides may be designed for use as probes and/or as primers in hybridization or PCR based detection methods, respectively.

Through the establishment of statistically significant correlations between the different single nucleotide polymorphic allelic forms of a complement receptor and various physiological or clinical manifestations of variable complement receptor function, the role of naturally occurring point mutations in clearing immune complex from the bloodstream is identified in homozygous genotype donors and in stable transfectants. These correlations are utilized to provide diagnostic utilities of the present invention. In practicing the present invention, preferably the correlations sought are those between particular complement receptor single nucleotide allelic polymorphs and the risk for developing any of the illustratively aforementioned diseases.

The term "allele" or "allelic form" is intended to mean an alternative version of a gene encoding the same functional protein but containing differences in nucleotide sequence relative to another version of the same gene.

The term "allelic polymorphism" or "allelic variant" is intended to mean a variation in the nucleotide sequence within a gene, wherein different individuals in a general population express different variants of the gene.

The term "allelic pattern" is intended to mean the identity of each of the two copies of a particular gene in a patient i.e., homozygosity or heterozygosity.

The term "allelic pattern" is used herein interchangeably with "genotype."

The term "genotyping" as used herein as being the process of determining the allelic patterns of a human individual.

The term "point mutation" as used herein is intended to mean a mutation involving a single nucleotide.

The term "silent mutation" as used herein is intended to mean a change of a nucleotide within a gene sequence that does not result in change in the coded amino acid sequence.

The term "missense mutation" as used herein is intended to mean a change of a nucleotide within a gene sequence that results in a change in the meaning of a codon, thereby changing the coded amino acid.

The term "frame shift mutation" as used herein is intended to mean a mutation involving the insertion or deletion of a single nucleotide that results in the remaining downstream sequence being transcribed or translated out of phase.

Examination of the DNA sequence encoding CR1 by direct sequence analysis shows a single nucleotide variation at position 5932. The single nucleotide polymorphism at position 5932 results in a missense codon, which translates to an alanine (A) to threonine (T) substitution at amino acid residue 1969 within the CR1 protein. Homozygous normal donors of each genotype at residue 1969 have been identified. FIG. 1 shows that 1969 A/A individuals have higher expression numbers of CR1 than homozygous T/T individuals. Correlations between CR1 expression on erythrocytes and donor genotype were made using quantitative flow cytometry following genotyping.

DNA was obtained from a donor and the presence of DNA sequences corresponding to a particular CR1 single nucleotide allelic polymorphism are determined. The DNA may be obtained from any cell source or body fluid containing intact nucleic acid bearing cells (expressing a complement receptor). DNA is extracted from the cell source using any of the numerous methods that are standard in the art. Once extracted, the DNA may be employed in the present invention without further manipulation. Direct sequencing is accomplished by chemical sequencing, using the Maxam-Gilbert method. It is appreciated that alternate sequencing methods such as enzymatic sequencing by way of methods such as the Sanger method are also operative herein and are described in application Ser. No 60/094,096, filed Jul. 24, 1998.

Once an individual has been genotyped, erythrocytes are exposed separately to anti-CR1 mAb species YZ1, E11, and 3D9. Fluorescence intensity associated with standardized cell populations correlates with copy number expression of CR1.

Standard analytical flow cytometry using one to four colors was performed on a FACScan flow cytometer (Becton-Dickinson). Sorting of cell lines is performed on a FACS-Vantage (Becton-Dickinson).

By extension of the flow cytometry process, a study was conducted to determine the distribution of CR1 1969 genotypes and 1969 allele frequencies. A control group consisted of healthy individuals and rheumatoid arthritis patients. The results from these groups were compared to the genotype distributions and allele frequencies for SLE patients. An over representation of the 1969 T allele in SLE patients is noted in Table 1.

TABLE 1

Distribution of CR1 Alleles in SLE Patients

|  | Normal + RA Comparison (N = 70) | SLE patients (N = 30) |
| --- | --- | --- |
| Genotype |  |  |
| 1969 A/A | 45 (64%) | 18 (60%) |
| 1969 A/T | 23 (33%) | 9 (30%) |
| 1969 T/T | 2 (3%) | 3 (10%) |
| Allele frequency |  |  |
| 1969 A | 0.81 | 0.75 |
| 1969 T | 0.19 | 0.25 |

The correlation of various single nucleotide polymorphisms in individuals including the 1969 naturally occurring A/T polymorph in CR1 as well as other single nucleotide polymorphs in CR1 and CR2 are correlated to cis-acting Hind III RFLP and the severity or susceptibility of individuals in SLE diathesis. In this way relative importance of specific single nucleotide polymorphs in disease progression is assessed.

Any patents, applications or publications mentioned in the specification are indicative of the levels of those skilled in the art to which the invention pertains. These patents and publications are herein incorporated by reference to the same extent as if each individual publication or patent was specifically and individually indicated to be incorporated by reference.

What is claimed is:

1. A method for determining CR1 alleles specific to an individual human, said method comprising: determining the identity of nucleotide 5932 in DNA encoding CR1, said DNA obtained from said individual human.

2. The method of claim 1 wherein said identity of nucleotide 5932 affects C3b binding by a CR1 receptor.

3. The method of claim 1 wherein said identity of nucleotide 5932 affects C4b binding by a CR1 receptor.

4. A method of predicting a human immunoresponse to systemic lupus erythematosus, said method comprising:

establishing a correlation between a CR1 genotype, wherein said CR1 genotype is the identity of nucleotide 5932 in DNA encoding CR1 and clinical outcome of said systemic lupus erythematosus;

genotyping a patient to determine the identity of nucleotide 5932 in DNA encoding CR1 to yield a patient CR1 genotype, said DNA obtained from said patient;

comparing said CR1 genotype with said patient CR1 genotype; and determining clinical outcome for said patient based on said patient CR1 genotype.

5. The method of claim 4 wherein said complement receptor is CR1.

* * * * *